US007612110B2

(12) United States Patent
Joshi et al.

(10) Patent No.: US 7,612,110 B2
(45) Date of Patent: *Nov. 3, 2009

(54) UTILIZATION OF DIALKYLFUMARATES

(75) Inventors: Rajendra Kumar Joshi, Zürich (CH); Hans-Peter Strebel, Muri (CH)

(73) Assignee: Biogen Idec International AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/765,563

(22) Filed: Jun. 20, 2007

(65) Prior Publication Data

US 2007/0248662 A1 Oct. 25, 2007

Related U.S. Application Data

(62) Division of application No. 10/197,077, filed on Jul. 17, 2002, now Pat. No. 7,320,999, which is a division of application No. 09/831,620, filed as application No. PCT/EP99/08215 on Oct. 29, 1999, now Pat. No. 6,509,376.

(30) Foreign Application Priority Data

Nov. 19, 1998 (DE) ................................ 198 53 487

(51) Int. Cl.
*A61K 31/225* (2006.01)
(52) U.S. Cl. .................. 514/547; 514/825; 514/960
(58) Field of Classification Search ................ 514/547, 514/960
See application file for complete search history.

(56) References Cited

U.S. PATENT DOCUMENTS

| | | | |
|---|---|---|---|
| 3,832,287 A | 8/1974 | Gale et al. | |
| 4,515,974 A | 5/1985 | Zecher et al. | |
| 4,746,668 A | 5/1988 | Sato et al. | |
| 4,851,439 A | 7/1989 | Speiser et al. | |
| 4,959,389 A * | 9/1990 | Speiser et al. | 514/494 |
| 5,149,695 A | 9/1992 | Speiser et al. | |
| 5,214,196 A | 5/1993 | Blank | |
| 5,242,905 A | 9/1993 | Blank | |
| 5,359,128 A | 10/1994 | Blank | |
| 5,424,332 A | 6/1995 | Speiser et al. | |
| 5,451,667 A | 9/1995 | Speiser et al. | |
| 5,538,968 A | 7/1996 | Chiesi et al. | |
| 5,548,059 A | 8/1996 | Bayley et al. | |
| 5,589,504 A | 12/1996 | Dannenburg et al. | |
| 5,972,363 A | 10/1999 | Clikeman et al. | |
| 6,277,882 B1 * | 8/2001 | Joshi et al. | 514/547 |
| 6,355,676 B1 * | 3/2002 | Joshi et al. | 514/494 |
| 6,359,003 B1 | 3/2002 | Joshi et al. | |
| 6,436,992 B1 * | 8/2002 | Joshi et al. | 514/547 |
| 6,509,376 B1 * | 1/2003 | Joshi et al. | 514/547 |
| 2003/0013761 A1 | 1/2003 | Joshi et al. | |
| 2004/0054001 A1 | 3/2004 | Joshi et al. | |
| 2006/0069161 A1 | 3/2006 | Lee et al. | |
| 2007/0248663 A1 | 10/2007 | Joshi et al. | |
| 2008/0233185 A1 | 9/2008 | Joshi et al. | |

FOREIGN PATENT DOCUMENTS

| | | |
|---|---|---|
| CA | 2248955 | 8/2001 |
| CA | 2248955 C * | 8/2001 |
| CN | 1125141 | 6/1996 |
| DE | 25 30 372 A1 | 1/1977 |
| DE | 26 21 214 A1 | 11/1977 |
| DE | 35 31597 | 3/1987 |
| DE | 38 34794 A1 | 4/1990 |
| EP | 0 188749 A2 | 7/1986 |
| EP | 0 312697 | 4/1989 |
| EP | 0 518388 | 12/1992 |
| EP | 0 793966 | 9/1997 |
| GB | 1 216699 | 12/1970 |
| GB | 1 422726 | 1/1976 |
| GB | 2 291422 | 1/1996 |
| WO | WO 89/01930 A1 | 3/1989 |
| WO | WO 94/28883 | 12/1994 |
| WO | WO 95/25102 | 9/1995 |
| WO | WO 96/01122 | 1/1996 |
| WO | WO 96/02244 | 2/1996 |
| WO | WO 96/27369 | 9/1996 |
| WO | WO 97/48400 | 12/1997 |
| WO | WO 98/04290 | 2/1998 |
| WO | WO 98/27970 | 7/1998 |
| WO | WO 98/52549 | 11/1998 |

(Continued)

OTHER PUBLICATIONS

Rao et al., "Antihepatotoxic activity of monomethyl fumarate isolated from *Fumaria indica*", Journal of Ethnopharmacology, vol. 60, No. 3, pp. 207-213 (Apr. 1998).*

(Continued)

*Primary Examiner*—Kevin Weddington
(74) *Attorney, Agent, or Firm*—Finnegan, Henderson, Farabow, Garrett & Dunner, L.L.P.

(57) ABSTRACT

The present invention relates to the use of certain dialkyl fumarates for the preparation of pharmaceutical preparations for use in transplantation medicine or for the therapy of autoimmune diseases and said compositions in the form of micro-tablets or pellets. For this purpose, the dialkyl fumarates may also be used in combination with conventional preparations used in transplantation medicine and immunosuppressive agents, especially cyclosporines.

29 Claims, No Drawings

FOREIGN PATENT DOCUMENTS

| | | |
|---|---|---|
| WO | WO 99/21565 | 5/1999 |
| WO | WO 01/59072 | 8/2001 |
| WO | WO 02/02190 | 1/2002 |
| WO | WO 03/032969 | 4/2003 |
| WO | WO 2004/096216 | 11/2004 |
| WO | WO 2005/027899 | 3/2005 |
| WO | WO 2005/044272 | 5/2005 |
| WO | WO 2006/037342 | 4/2006 |
| WO | WO 2006/050730 | 5/2006 |
| WO | WO 2006/055871 | 5/2006 |

OTHER PUBLICATIONS www.en.wikipedia.org/wiki/Polyarthritis (2008).*

Andersson et al., "Cytokine profile in interferon-β treated multiple sclerosis patients: reduction of interleukin-10 mRNA expressing cells in peripheral blood," Eur. J. Neurol. 4: 567-571, 1997.

Becanovic et al., "Paradoxical effects or arthritis-regulating chromosome 4 regions on myelin oligodendrocyte glycoprotein-induced encephalomyelitis in congenic rats," Eur. J. Immunol. 33: 1907-1916, 2003.

Correale et al., "Sulfasalazine aggravates experimental autoimmune encephalomyelitis and causes an increase in the number of autoreactive T cells," J. Neuroimmunol. 34:109-120, 1991.

Dahlman et al., "Quantitative trait loci disposing for both experimental arthritis and encephalomyelitis in the DA rat; impact on severity of myelin oligodendrocyte glycoprotein-induced experimental autoimmune encephalomyelitis and antibody isotype pattern," Eur. J. Immunol. 28:2188-2196, 1998.

De Graaf et al., "MHC Class 11 Isotype- and Allele-Specific Attenuation of Experimental Autoimmune Encephalomyelitis," J. Immunol., 173: 2792-2802, 2004.

Di Marco et al., "Curative effects of recombinant human Interleukin-6 in DA rats with protracted relapsing experimental allergic encephalomyelitis," J. Neuroimmunol. 116: 168-177, 2001.

Djerbi et al., "Expression of the Long Form of Human FLIP by Retroviral Gene Transfer of Hemopoietic Stem Cells Exacerbates Experimental Autoimmune Encephalomyelitis," J. Immunol. 170: 2064-2073, 2003.

Gielen et al., "Expression of T cell immunoglobulin- and mucin-domain-containing molecules-1 and -3 (TIM-1 and -3) in the rat nervous and immune systems," J. Neuroimmunol., 164: 93-104, 2005.

Guggenmos et al., "Antibody Cross-Reactivity between Myelin Oligodendrocyte Glycoprotein and the Milk Protein Butyrophilin in Multiple Sclerosis," J. Immunol. 172: 661-668, 2004.

Issazadeh et al., "Cytokine production in the central nervous system of Lewis rats with experimental autoimmune encephalomyelitis: dynamics of mRNA expression for interleukin-10, interleukin-12, cytolysin, tumor necrosis factor α and tumor necrosis factor β," J. Neuroimmunol. 61: 205-212, 1995.

Issazadeh et al., "Interferon γ, Interleukin 4 and Transforming Growth Factor β in Experimental Autoimmune Encephalomyelitis in Lewis Rats: Dynamics of Cellular mRNA Expression in the Central Nervous System and Lymphoid Cells," J. Neurosci. Res. 40: 579-590, 1995.

Issazadeh et al., "Cytokines in relapsing experimental autoimmune encephalomyelitis in DA rats: persistent mRNA expression of proinflammatory cytokines and absent expression of interleukin-10 and transforming growth factor-β," J. Neuroimmunol. 69: 103-115, 1996.

Issazadeh et al., "Major histocompatibility complex-controlled protective influences on experimental autoimmune encephalomyelitis are peptide specific," Eur. J. lmmunol. 27: 1584-1587, 1997.

Khademi et al., "Reduction of both pro- and anti-inflammatory cytokines after 6 months of interferon beta-1a treatment of multiple sclerosis," J. Neuroimmunol. 103:202-210, 2000.

Khademi et al., "T Cell Ig- and Mucin-Domain-Containing Molecule-3 (TIM-3) and TIM-1 Molecules Are Differentially Expressed on Human Th1 and Th2 Cells and in Cerebrospinal Fluid-Derived Mononuclear Cells in Multiple Sclerosis," J. Immunol. 172: 7169-7176, 2004.

Khademi et al., "Induction of systemic TNFα Expression in Natalizumab-treated multiple sclerosis," Eur. J. Neurol., 15: 309-12, 2008.

Kjellén et al., "Genetic influence on disease course and cytokine response in relapsing experimental allergic encephalomyelitis," Int. Immunol. 10: 333-340, 1998.

Krakauer et al., "Dynamic T-lymphocyte Chemokine Receptor Expression Induced by Interferon-beta Therapy in Multiple Sclerosis," Scand. J. lmmunol. 64: 155-163, 2006.

Link et al., "Virus-reactive and autoreactive T cells are accumulated in cerebrospinal fluid in multiple sclerosis," J. Neuroimmunol. 38: 63-73, 1992.

Link et al., "Organ-specific Autoantigens Induce Transforming Growth Factor-β mRNA Expression in Mononuclear Cells in Multiple Sclerosis and Myasthenia Gravis," Annals Neurol. 35: 197-203, 1994.

Link et al., "Organ-specific autoantigens induce interferon-γ and interleukin-4 mRNA expression in mononuclear cells in multiple sclerosis and myasthenia gravis," Neurology 44: 728-734, 1994.

Link et al., "Optic neuritis is associated with myelin basic protein and proteolipid protein reactive cells producing interferon-γ, interleukin-4 and transforming growth factor-β," J. Neuroimmunol. 49:9-18, 1994.

Link et al., "Increased Transforming Growth Factor-β, Interleukin-4, and Interferon-γ in Multiple Sclerosis," Ann. Neurol. 36: 379-386, 1994.

Lobell et al., "Vaccination with DNA Encoding an Immunodominant Myelin Basic Protein Peptide Targeted to Fc of Immunoglobulin G Suppresses Experimental Autoimmune Encephalomyelitis," J. Exp. Med. 187: 1543-1548, 1998.

Lobell et al., "Presence of CpG DNA and the Local Cytokine Milieu Determine the Efficacy of Suppressive DNA Vaccination in Experimental Autoimmune Encephalomyelitis," J. Immunol. 163: 4754-4762, 1999.

Lobell et al., "Suppressive DNA Vaccination in Myelin Oligodendrocyte Glycoprotein Peptide-Induced Experimental Autoimmune Encephalomyelitis Involves a T1-Biased Immune Response," J. Immunol. 170: 1806-1813, 2003.

Lorentzen et al., "Protracted, relapsing and demyelinating experimental autoimmune encephalomyelitis in DA rats immunized with syngeneic spinal cord and incomplete Freund's adjuvant," J. Neuroimmunol. 63: 193-205, 1995.

Lorentzen et al., "Genetic analysis of inflammation, cytokine mRNA expression and disease course of relapsing experimental autoimmune encephalomyelitis in DA rats," J. Neuroimmunol. 80: 31-37, 1997.

Matusevicius et al., "Autoantigen-induced IL-13 mRNA expression is increased in blood mononuclear cells in myasthenia gravis and multiple sclerosis," Eur. J. Neurol. 4: 468-475, 1997.

Muhallab et al., "Intra-CNS activation by antigen-specific T lymphocytes in experimental autoimmune encephalomyelitis," J Neuroimmunol. 113: 202-211, 2001.

Mustafa et al., "T cell immunity and interferon-γ secretion during experimental allergic encephalomyelitis in Lewis rats," J. Neuroimmunol. 31: 165-177, 1991.

Mustafa et al., "Immunopharmacologic Modulation of Experimental Allergic Encephomyelitis: Low-Dose Cyclosporin-A Treatment Causes Disease Relapse and Increased Systemic T and B Cell-Mediated Myelin-Directed Autoimmunity," Scand. J. Immunol. 38: 499-507, 1993.

Mustafa et al., "The major histocompatibility complex influences myelin basic protein 63-88-induced T cell cytokine profile and experimental autoimmune encephalomyelitis," Eur. J. Immunol. 23: 3089-3095, 1993.

Mustafa et al., "Protective Influences on Experimental Autoimmune Encephalomyelitis by MHC Class I and Class II Alleles," J. Immunol. 153: 3337-3344, 1994.

Navikas et al., "Increased mRNA Expression of IL-10 in Mononuclear Cells in Multiple Sclerosis and Optic Neuritis," Scand. J. Immunol. 41: 171-178, 1995.

Navikas et al., "Augmented expression of tumour necrosis factor-α and lymphotoxin in mononuclear cells in multiple sclerosis and optic neuritis," Brain 119: 213-223, 1996.

Olsson et al., "Autoreactive T Lymphocytes in Multiple Sclerosis Determined by Antigen-induced Secretion of Interferon-γ," J. Clin. Invest. 86: 981-985, 1990.

Olsson et al., "Increased numbers of T cells recognizing multiple myelin basic protein epitopes in multiple sclerosis," Eur. J. Immunol. 22: 1083-1087, 1992.

Olsson, "Cytokines in neuroinflammatory disease: role of myelin autoreactive T cell production of interferon-gamma," J. Neuroimmunol. 40: 211-218, 1992.

Olsson, "Cerebrospinal Fluid," Ann. Neurol. 36: S100-S102, 1994.

Olsson, "Role of cytokines in multiple sclerosis and experimental autoimmune encephalomyelitis," Eur. J. Neurol. 1: 7-19, 1994.

Olsson, "Critical Influences of the Cytokine Orchestration on the Outcome of Myelin Antigen Specific T Cell Autoimmunity in Experimental Autoimmune Encephalomyelitis and Multiple Sclerosis," Immunological Reviews 144: 245-268, 1995.

Olsson, "Chapter 6: Cytokines in Multiple Sclerosis and Its Experimental Models," from *Neuroscience Intelligence Unit 5: T-Cell Autoimmunity and Multiple Sclerosis*, Ed. M. Londei, R.G. Landes Company, Austin, TX, 1999, pp. 91-112.

Olsson, "15: Future prospects of cytokines in the pathogenesis and management of multiple sclerosis," vol. 2 edited by Aksel Siva, Jürg Kesserlring and Alan J. Thompson, Martin Dunitz Publishers Ltd, London, UK, 1999, pp. 139-150.

Olsson et al., "Chapter 22: MHC and Non-MHC Genetics of Experimental Autoimmune Encephalomyelitis," from *From Basic Immunology to Immune-Mediated Demyelination*, Eds G. Martino and L. Adorini, Springer-Verlag, Milan, Italy, 1999, pp. 246-264.

Olsson et al., "Genetics of rat neuroinflammation," J Neuroimmunol. 107: 191-200, 2000.

Olsson et al., "Depletion of Vβ5.2/5.3 T cells with a humanized antibody in patients with multiple sclerosis," Eur. J. Neurol. 9: 153-164, 2002.

Olsson et al., "Harm or heal—divergent effects of autoimmune neuroinflammation?," Trends in Immunol. 24: 5-6, 2003.

Robinson et al., "Protein microarrays guide tolerizing DNA vaccine treatment of autoimmune encephalomyelitis," Nat. Biotech., 21: 1033-1039, 2003.

Ruuls et al., "The Length of Treatment Determines Whether IFN-β Prevents or Aggravates Experimental Autoimmune Encephalomyelitis in Lewis Rats," J. Immunol. 157: 5721-5731, 1996.

Söderström et al., "T Cells Recognizing Multiple Peptides of Myelin Basic Protein are Found in Blood and Enriched in Cerebrospinal fluid in Optic Neuritis and Multiple Sclerosis," Scand. J. Immunol. 37: 355-368, 1993.

Sun et al., "Treatment of experimental autoimmune encephalomyelitis by feeding myelin basic protein conjugated to cholera toxin B subunit," Proc. Natl. Acad. Sci. USA 93: 7196-7201, 1996.

Wallström et al., "Memantine abrogates neurological deficits, but not CNS inflammation, in Lewis rat experimental autoimmune encephalomyelitis," J. Neurol. Sci. 137: 89-96, 1996.

Wallström et al., "Increased reactivity to myelin oligodendrocyte glycoprotein peptides and epitope mapping in HLA DR2(15)+ multiple sclerosis," Eur. J. Immunol. 28: 3329-3335, 1998.

Wang et al., "Myelin antigen reactive T cells in cerebrovascular diseases," Clin. Exp. Immunol. 88: 157-162, 1992.

Weissert et al., Protective DNA vaccination against organ-specific autoimmunity is highly specific and discriminates between single amino acid substitutions in the peptide autoantigen. PNAS 97:1689-1694, 2000.

Balashov et al., "Defective regulation of IFNγ and IL-12 by endogenous IL-10 in progressive MS," Neurology 55: 192-198, 2000.

Bettelli and Nicholson, "The Role of Cytokines in Experimental Autoimmune Encephalomyelitis," Archivum Immunologiae et Therapiae Experimentalis 48: 389-398, 2000.

Brown and Kraft, "Multiple Sclerosis: A Paradigm Shift," Phys. Med. Rehabil. Clin. N. Am. 16: xvii-xx, 2005.

Cannella et al., "IL-10 Fails to Abrogate Experimental Autoimmune Encephalomyelitis," J. Neuroscience Research 45: 735-746, 1996.

Dal Canto et al., "Local Delivery of TNF by Retrovirus-Transduced T Lymphocytes Exacerbates Experimental Autoimmune Encephalomyelitis," Clinical Immunol. 90: 10-14, 1999.

Robinson Jr. of Darby & Darby, Letter dated Dec. 11, 2007, to Susan H. Alexander, Esq., General Counsel, Biogen Idec.

Del Prete, G., "The Concept of Type-1 and Type-2 Helper T Cells and Their Cytokines in Humans," Intern. Rev. Immunol. 16: 427-455, 1998.

Di Rosa et al., "Lack of Th2 cytokine increase during spontaneous remission of experimental allergic encephalomyelitis," Eur. J. Immunol. 28: 3893-3903, 1998.

Ferber et al., "Mice with a Disrupted IFN-γ Gene Are Susceptible to the Induction of Experimental Autoimmune Encephalomyelitis (EAE)," J. Immunol. 156: 5-7, 1996.

Ferrante et al., "Cytokine Production and Surface Marker Expression in Acute and Stable Multiple Sclerosis: Altered IL-12 Production and Augmented Signaling Lymphocytic Activation Molecule (SLAM)—Expressing Lymphocytes in Acute Multiple Sclerosis," J. Immunol. 160: 1514-1521, 1998.

Furlan et al., "Interferon-β treatment in multiple sclerosis patients decreases the number of circulating T cells producing interferon-γ and interleukin-4," J. Neuroimmunol. 111: 86-92, 2000.

Galli et al., "Macrophage-derived chemokine production by activated human T cells in vitro and in vivo: preferential association with the production of type 2 cytokines," Eur. J. Immunol. 30: 204-210, 2000.

Genain et al., "Late Complications of Immune Deviation Therapy in a Nonhuman Primate," Science 274: 2054-2057, 1996.

Gijbels et al., "Administration of Neutralizing Antibodies to Interleukin-6 (IL-6) Reduces Experimental Autoimmune Encephalomyelitis and Is Associated with Elevated Levels of IL-6 Bioactivity in Central Nervous System and Circulation," Molecular Medicine 1: 795-805, 1995.

Giovannoni and Miller, "Multiple sclerosis and its treatment," J. R. Coll. Physicians Lond. 33: 315-322, 1999.

Hemmer et al., "Cytokine Phenotype of Human Autoreactive T Cell Clones Specific for the Immunodominant Myelin Basic Protein Peptide (83-99)," J. Neuroscience Res. 45: 852-862, 1996.

Hintzen and Polman, "Th-cell modulation in multiple sclerosis," Immunol. Today 18: 507-508, 1997.

Hultgren et al., "Genetic Absence of γ-Interferon Delays but Does Not Prevent Diabetes in NOD Mice," Diabetes 45: 812-817, 1996.

Krakowski et al., "Interferon-γ confers resistance to experimental allergic encephalomyelitis," Eur. J. Immunol. 16: 1641-1646, 1996.

Lafaille et al., "Myelin Basic Protein-specific T Helper 2 (Th2) Cells Cause Experimental Autoimmune Encephalomyelitis in Immunodeficient Hosts Rather than Protect Them from the Disease," J. Exp. Med. 186: 307-312, 1997.

Lafaille J., "The Role of Helper T Cell Subsets in Autoimmune Diseases," Cytokine & Growth Factor Review, 9: 139-151, 1998.

Laman et al., "Balancing the Th1/Th2 concept in multiple sclerosis," Immunol. Today 19: 489-490, 1998.

The Lenercept Mutliple Sclerosis Study Group and the University of British Columbia MS/MRI Analysis Group, "TNF neutralization in MS: Results of a randomized, placebo-controlled multicenter study," Neurol. 53: 457-465, 1999.

Liedtke et al., "Effective Treatment of Models of Multiple Sclerosis by Matrix Metalloproteinase Inhibitors," Ann. Neurol. 44: 35-46, 1998.

Link, H., "The cytokine storm in multiple sclerosis," Mult. Scler. 4: 12-15, 1998.

Lopez et al., "Interferon γ, IL2, IL4, IL10 and TNFα Secretions in Multiple Sclerosis Patients Treated with an Anti-CD4 Monoclonal Antibody," Autoimmunity 29: 87-92, 1999.

Lyons et al., "Pathogenesis of acute passive murine encephalomyelitis II. Th1 phenotype of the inducing population is not sufficient to cause disease," J. Neuroimmunol. 93: 26-36, 1999.

Määttä et al., "Neutrophils secreting tumor necrosis factor alpha infiltrate the central nervous system of BALB/c mice with experimental autoimmune encephalomyelitis," J. Neuroimmunol. 90: 162-175, 1998.

Martin et al., "T helper cell differentiation in multiple sclerosis and autoimmunity," Immunol. Today 19: 495-498, 1998.

Mattner et al., "Inhibition of Th1 development and treatment of chronic-relapsing experimental allergic encephalomyelitis by a non-hypercalcemic analogue of 1,25-dihydroxyvitamin $D_3$," Eur. J. Immunol. 30: 498-508, 2000.

O'Garra et al., "$CD4^+$T-cell subsets in autoimmunity," Current Opinion in Immunol. 9: 872-883, 1997.

Olsson, T., "Cytokine-producing cells in experimental autoimmune encephalomyelitis and multiple sclerosis," Neurology 45: S11-S15, 1995.

Panitch et al., "Exacerbations of Multiple Sclerosis in Patients Treated With Gamma Interferon," The Lancet 1:893-895, 1987.

Perrella et al., "Interleukin-10 and IFN-α in multiple sclerosis : is there a balance ?," J. Neurovirol. 3 (Suppl): P17, 1997.

Pette et al., "Differential effects of phosphodiesterase type 4-specific inhibition on human autoreactive myelin-specific T cell clones," J. of Neuroimmunol. 98: 147-156, 1999.

Ristori et al., "T cell response to myelin basic protein before and after treatment with interferon beta in multiple sclerosis," J. Neuroimmunol. 99: 91-96, 1999.

Rohowky-Kochan et al., "Impaired interleukin-12 production in multiple sclerosis patients," Mult. Scler. 4: 327-334, 1999.

Rohowky-Kochan et al., Cytokine secretion profile of myelin basic protein-specific T cells in multiple sclerosis, Mult. Scler. 6: 69-77, 2000.

Romagnani S., "The Th1/Th2 paradigm," Immunol. Today 18: 263-266, 1997.

Rook et al., "Bacterial vaccines for the treatment of multiple sclerosis and other autoimmune diseases," Immunol. Today 21: 503-508, 2000.

Samoilova et al., "Experimental Autoimmune Encephalomyelitis in Intercellular Adhesion Molecule-1-Deficient Mice," Cell. Immunol. 190: 83-89, 1998.

Singh et al., "The Paradigm of Th1 and Th2 Cytokines, It's Relevance to Autoimmunity and Allergy," Immunol. Res. 20: 147-161, 1999.

Sinigaglia et al., "Type I interferons and the Th1/Th2 paradigm," Developmental and Comparative Immunol. 23: 657-663, 1999.

Smeltz et al., "Concordance and Contradiction Concerning Cytokines and Chemokines in Experimental Demyelinating Disease," J. Neuroscience Res. 51: 147-153 1998.

Zhu et al., "Cytokine production and the pathogenesis of experimental autoimmune neuritis and Guillain—Barré syndrome," J. Neuroimmunol. 84: 40-52, 1998.

Zipp, F., "No Evidence for Generation of Th-2-like MBP-Specific T-Cell Lines by Blockade of the Costimulatory Molecule B7-1," Scand. J. Immunol. 52: 510-514, 2000.

Anderson et al., Contact Dermatitis, 16:55-78, 1987.

DeJong et al., European Journal of Immunology, 26:2067-2074, 1996.

Dücker et al., H+Z Zeitschrift fur Haut., 65:734-736, 1989, abstract.

Fliegner et al., Hautarzt, 43:554-560, 1992, abstract.

Ghoreschi et al., Arch. Dermatol. Res., 296:P110, 2005.

Ghoreschi et al., Arch. Dermatol. Res., 294:28, 2002.

Ghoreschi et al., Current Drug Targets: Inflammation and Allergy 3:193-198, 2004.

Hunziker et al., "Is Psoriasis an Autoimmune Disease?", excerpt from "Therapeutische Umschau", Derm. Clinic of Univ. Berne, 50:110-113, 1993.

International Search Report for PCT/EP99/08215 dated Jun. 26, 2000.

Kiehl et al., Acta Derm. Venerol., 72:253-255, 1992.

Kolbach et al., J. Am. Acad. Derm., 27:769-771, 1992.

Lahti et al., Contact Dermatitis, 12:139-140, 1985.

Merck Index, 10th Ed., 1983 Abs. 2748.

Nieboer et al., J. Am. Acad. Derm., 20:601-608, 1989.

Peeters et al., Ned. Tijdschr. Geneeskd., 136:2428-2431, 1992, abstract.

Sadjak et al., Deutsch Med. Wochenschr., 116:478, 1991.

Schilling et al., Clinical and Experimental Immunology, 145:101-107, 2006.

Schilling et al., Aktuelle Rheumatologie, 24(6):174-179, 1999, abstract.

Schimrigk et al., European J. of Neurology: The Official Journal of the European Federation of Neurological Societies, 13:604-610, 2006.

Sebok et al., Skin Pharm., 9:99-103, 1996.

Thio et al., Br. J. Dermatol., 131:865-861, 1994.

English Language Derwent Abstract for CN 1125141, date unavailable.

English Language Derwent Abstract for DE 35 31 597, date unavailable.

Altmeyer et al., "Systemische Therapie der Psoriasis", T & E Dermatologie Jg., 1997, vol. 27, pp. 380-382, 384—not translated.

Bacharach-Buhles et al., "Fumaric Acid Esters (FAEs) Suppress CD 15- and ODP 4-positive Cells in Psoriasis", Acta Derm Venerol (Stockh); 1994; Suppl. 186: 79-82.

Ockenfels et al., "The antipsoriatic agent dimethytfumarate immunomodulates T-cell cytokine secretion and inhibits cytokines of the psoriatic cytokine network," Brit. J. Dermatol. 139: 390-395, 1998.

Gasser et al., "Host Vs Graft and Graft Vs Host Reactions After Allogenic Heterotopic Small Bowel Transplantation in the Rat", Transplantation Proceedings, vol. 24, No. 3, Jun. 1992, pp. 1128-1129.

Nathens et al., "The Glutathione Depleting Agent Diethylmaleate Prolongs Renal Allograft Survival", Journal of Surgical Research, vol. 77, 1998, pp. 75-79.

Nibbering et al., "Intracellular Signalling by Binding Sites for the Antipsoratic Agent Monomethylfumarate on Human Granulocytes", British J. Dermatol., 1997, vol. 137, pp. 65-75.

Nibbering, PH, "Effects of Monomethylfumarate on Human Granulocytes", Journal of Investigative Dermatology, 1993, vol. 101, pp. 37-42.

Sebok et al., "Antiproliferative and Cytotoxic profiles of Antipsoriatic Fumaric Acid Derivatives in Keratinocyte Cultures," European Journal of Pharm., Environ. Toxicol. Pharmacol. Sect., 1994, vol. 270, pp. 79-87.

Schwinghammer et al., "Pharmacologic prophylaxis of acute graft-versus-host disease after allogeneic marrow transplantation", Therapy Reviews, Clinical Pharmacy, vol. 12, Oct. 1993, pp. 736-761.

Medline Abstract of Bayard et al., "Peroral long-term treatment of psoriasis using fumaric acid derivatives", Hautarzt, May 1987, 38(5), pp. 279-285.

"Merck Manual", 1987, Merck XP-002141006, p. 327, paragraph 2-paragraph 6.

Immunmodulation durch Fumaderm, Das richtungsweisende Konzept, Charite-Berlin, Hautklinik, Symposium, 1.-3. Nov. 1996, 28 pages, 4 page english translation of pp. 23-24.

Amamoto et al., "Effect of E-64, Thiol Protease Inhibitor on the Secondary Anti-SRBC Response In Vitro", Microbiol. Immunol., vol. 28(1), 1984, pp. 85-97.

Barrett et al., "L-trans-Epoxysuccinyl-leucylamido(4-guanidino)butane (E-64) and its analogues as inhibitors of cysteine proteinases including cathepsins B, H and L", Biochem. J., 1982, vol. 201, pp. 189-198.

Bellier et al., "Replacement of Glycine with Dicarbonyl and Related Moieties in Analogues of the C-Terminal Pentapeptide of Cholecystokinin: $CCK_2$ Agonists Displaying a Novel Binding Mode", J. Med. Chem., vol. 43, 2000, pp. 3614-3623.

Birch et al., "Metabolites of *Aspergillus indicus*: The Structure and Some Aspects of the Biosynthesis of Dihydrocanadensolide", Aust. J. Chem., 1968, vol. 21, pp. 2775-2784.

Choo et al., "Design and Synthesis of α,β-unsaturated Carbonyl Compounds as Potential ACE Inhibitors", Short Communication, Eur. J. Med. Chem., vol. 35, 2000, pp. 643-648.

Dethlefsen, L.A., "Toxic Effects of Acute Glutathione Depletion by Buthionine Sulfoximine and Dimethylfumarate on Murine Mammary Carcinoma Cells", Radiation Research, vol. 114, 1988, pp. 215-224.

Galpin et al., "The Synthesis of an Insulin Active Site Analogue", Tetrahedron, vol. 39, No. 1, 1983, pp. 149-158.

Gerhard et al., "The Free Energy Change of restricting A Bond Rotation in the Binding of Peptide Analogues to Vancomycin Group Antibiotics", Bioorganic & Medicinal Chemistry Letters, vol. 3, No. 5, 1993, pp. 803-808.

Gordon et al., "Induction of NAD(P)H:quinone reductase in human peripheral blood lymphocytes", Carcinogenesis, vol. 12 (12), 1991, pp. 2393-2396.

Griehl et al., "α-Aspartyl Peptides by Addition of Amines to N-Maleylamino Acid Derivatives", Chemistry of Peptides and Proteins, 1993, 5/6(pt. A), pp. 99-103.

Hildebrandt, H., "Pschyrembel Klinisches Woerterbuch Ed. 258", 1998, Walter de Gruyter, New York, XP 002234302, p. 182, col. 1, paragraph 2 and p. 1469, col. 1, paragraphy 16-col. 2, paragraphy 1. Not translated.

Hohenneger et al., "Nephrotoxicity of Fumaric Acid Monoethylester (FA ME)", Advances in Experimental Medicine and Biology, US 1989, vol. 252, pp. 265-272.

Holroyd et al., "Rational Design and Binding of Modified Cell-Wall Peptides to Vancomycin-Group Antibiotics: Factorising Free Energy Contributions to Binding", Tetrahedron, vol. 49, No. 41, 1993, pp. 9171-9182.

Kamiyama et al., "Ro 09-1679, A Novel Thrombin Inhibitor", The Journal of Antibiotics, vol. 45, No. 3, Mar. 1992, pp. 424-427.

Krstenansky et al., "Development of MDL 28,050, a Small Stable Antithrombin Agent Based on a Functional Domain of the Leech Protein, Hirudin", Thrombosis and Haemostasis, vol. 63, No. 2, 1990, Stuttgart, De.

Kuroda et al., "Fumaric Acid Enhances DNA Synthesis of Rat Hepatocytes by Counter Acting the Toxicities of Mitomycin C and Aflatoxin $B_1$", Jpn. J. Cancer Res. (Gann), Aug. 1986, vol. 77, pp. 750-758.

Kuroda et al., "Inhibitory Effect of Capsella-bursa-pastoris extract on Growth of Ehrlich Solid Tumor in Mice", Cancer Research, vol. 36, 1976, abstract.

Langlois et al., "Synthesis of symmetrical pseudopeptides as potential inhibitors of the human immunodeficiency virus-1 protease", Eur. J. Med. Chem., vol. 29, 1994, pp. 639-647.

Lehnert et al., "Radiation Response of Drug-Resistant Variants of a Human Breast Cancer Cell Line: The Effect of Glutathione Depletion", Radiation Research, vol. 124, 1990, pp. 208-215.

Miller et al., "Posttranscriptional Down-Regulation of ras Oncogene Expression by Inhibitors of Cellular Glutathione", Molecular and Cellular Biology, Jul. 1993, vol. 13, No. 7, pp. 4416-4422.

Mrowietz, U., "Nephrotoxische Wirkung durch Fumarsaure", Hautarzt, 2000-51:615, Springer-Verlag 2000, pp. 615. Not translated.

Odom et al., "Cancer Chemoprotective Agents Inhibition of Human HT29 Colon Carcinoma Cell Proliferation is Reversed by N-Acetyl Cysteine", Proceedings of the American Assoc. for Cancer Research Annual, No. 41, Mar. 2000, pp. 342, XP008017517.

Ondrus et al., "A Simple Synthesis of Some analogues of Natural Antibiotics", Preliminary Communication, Chem. Papers, 51(3), 1997, pp. 164-166.

Orta et al., "Glutathione manipulation and the radiosensitivity of human tumour and fibroblast cell lines", Int. J. Radiat. Biol., 1995, vol. 68, No. 4, pp. 413-419.

Pearl et al., "Fumarate-enriched blood cardioplegia results in complete functional recovery of immature myocardium", Annals of Thoracic Surgery, vol. 57, No. 6, 1994, astract.

Peeters et al., "Fumaric Acid Therapy for Psoriatic Arthritis. A Randomized, Double-blind, Placebo-controlled Study", British Journal of Rheumatology, vol. XXXI, No. 7, Jul. 1992, pp. 502-504.

Pereira et al., "Use of azoxymethane-induced foci of aberrant crypts in rat colon to identify potential cancer chemopreventive agents", Carcinogenesis, vol. 15, No. 5, 1994, pp. 1049-1054.

Portoghese et al., "Synthesis and Biological Activity of Analogues of β-Chlornaltrexamine and β-Funaltrexamine at Opioid Receptors", J. of Medicinal Chem., vol. 29, No. 10, 1986, pp. 1861-1864.

Prochaska et al., "Elevation of Glutathione Levels by Phase II Enzyme Inducers: Lack of Inhibition of Human Immunodeficiency Virus Type 1 Replication in Chronically Infected Monocytoid Cells", Molecular Pharmacology, vol. 45, No. 5, 1994, pp. 916-921.

Prochaska et al., "Oltipraz, an inhibitor of human immunodeficiency virus type 1 replication", Proc. Natl. Acad. Sci., USA, vol. 90, May 1993, pp. 3953-3957.

Rao et al., "Chemoprevention of Azoxymethane-Induced Colon Cancer by Ascorbylpalmitate, Carbenoxolone, Dimethylfumarate and p-Methoxyphenol in Male F344 Rats", Anticancer Research, vol. 15, 1995, pp. 1199-1204.

Rao et al., "Antihepatotoxic activity of monomethyl fumarate isolated from *Fumaria indica*," J. of Ethnopharm. 60: 207-213, 1998.

Roodnat et al., "Akute Niereninsuffizienz bei der Behandlung der Psoriasis mit Fumarsaure-Estern", Schweiz. Med., Wschr., vol. 119, nr 2, 1989, pp. 826-830. Not translated.

Rossi et al., "Approach to the Use of Benzylpenicillinacylase for Configurational Correlations of Amino Compounds. 2. Hydrolysis of N-(p-Aminophenylacetyl) Derivatives of Some Chiral Primary Amines", J. Org. Chem., vol. 44, No. 13, 1979, pp. 2222-2225.

Schirmeister, T, "Aziridine-2,3-dicarboxylic Acid Derivatives as Inhibitors or Papain", Arch. Pharm. Pharm. Med. Chem., 329, 1996, pp. 239-244.

Schmidt et al., "Anti-psoriatic drug anthralin activates transcription factor NF-kappa-B in murine keratinocytes", Journal of Immunology, vol. 156, 1996, abstract.

Spencer et al., "Induction of Glutathione Transferases and NAD(P)H:Quinone Reductase by Fumaric Acid Derivatives in Rodent Cells and Tissues", Cancer Research, vol. 50, 1990, pp. 7871-7875.

Steele et al., "Preclinical Efficacy Evaluation of Potential Chemopreventive Agents in Animal Carcinogenesis Models: Methods and Results From the NCI Chemoprevention Drug Development Program", J. of Cellular Biochemistry, Supplement 20, 1994, pp. 32-54.

Su et al., "Reduction of $H_2O_2$-evoked, intracellular calcium increases in the rat N18-RE-105 neuronal cell line by pretreatment with an electrophilic antioxidant inducer", Neuroscience Letters, 273, 1999, pp. 109-112.

Subasinghe et al., "Synthesis of Acyclic and Dehydroaspartic Acid Analogues of Ac-Asp-Glu-OH and Their Inhibition of Rat Brain N-Acetylated α-linked Acidic Dipeptidase (NAALA Dipeptidase)", Journal of Medicinal Chemistry, vol. 33, No. 10., 1990, pp. 2734-2744.

Vandermeeren et al., "Dimethylfumarate is an Inhibitor of Cytokine-Induced Nuclear Translocation of NF-κB1, But not RelA in Normal Human Dermal Fibroblast Cells", The Journal of Investigative Dermatology, vol. 116, No. 1, Jan. 2001, pp. 124-130.

Vandermeeren et al., "Dimethylfumarate is an Inhibitor of Cytokine-Induced E-Selection, VCAM-1, and ICAM-1 Expression in Human Endothelial Cells", Biochemical and Biophysical Research Communications, vol. 234, 1997, pp. 19-23.

Wang et al., "Enhanced cytotoxicity of mitomycin C in human tumour cells with inducers of DT-diaphorase", British Journal of Cancer, vol. 80(8), 1999, pp. 1223-1230.

Weinmann et al., "Influence of Fumaric Acid Derivatives on T Lymphocytes in the Murine Model of HSV-I Keratitis", IOVS, vol. 41, No. 4, Mar. 15, 2000, XP008017516, pp. S146.

English Language Translation of PCT International Preliminary Examination Report for PCT/EP99/08215, completed Feb. 27, 2001.

Office Action mailed Mar. 22, 2004, in U.S. Appl. No. 10/197,077 (now U.S. Patent 7,320,999).

Response filed Aug. 6, 2004, in U.S. Appl. No. 10/197,077 (now U.S. Patent 7,320,999).

Notice of Noncompliant Amendment mailed Aug. 19, 2004, in U.S. Appl. No. 10/197,077 (now U.S. Patent 7,320,999).

Response filed Aug. 25, 2004, in U.S. Appl. No. 10/197,077 (now U.S. Patent 7,320,999).

Supplemental Amendment filed Nov. 22, 2004, in U.S. Appl. No. 10/197,077 (now U.S. Patent 7,320,999).

Notice of Noncompliant Amendment mailed Dec. 16, 2004, in U.S. Appl. No. 10/197,077 (now U.S. Patent 7,320,999).

Response to Notice of Noncompliant Amendment filed Jan. 5, 2005, in U.S. Appl. No. 10/197,077 (now U.S. Patent 7,320,999).

Office Action mailed Nov. 28, 2005, in U.S. Appl. No. 10/197,077 (now U.S. Patent 7,320,999).

Response filed Feb. 24, 2006, in U.S. Appl. No. 10/197,077 (now U.S. Patent 7,320,999).
Notice of Noncompliant Amendment mailed Mar. 1, 2006, in U.S. Appl. No. 10/197,077 (now U.S. Patent 7,320,999).
Response to Notice of Noncompliant Amendment (37 CFR 1.121) filed Mar. 10, 2006, in U.S. Appl. No. 10/197,077 (now U.S. Patent 7,320,999).
Office Action mailed Jun. 21, 2006, in U.S. Appl. No. 10/197,077 (now U.S. Patent 7,320,999).
Response to Restriction Requirement dated Jun. 21, 2006, filed Aug. 21, 2006, in U.S. Appl. No. 10/197,077 (now U.S. Patent 7,320,999).
Amendment filed Mar. 2, 2007, in U.S. Appl. No. 10/197,077 (now U.S. Patent 7,320,999).
Office Action mailed May 15, 2007, in U.S. Appl. No. 10/197,077 (now U.S. Patent 7,320,999).
Interview Summary for interview held Aug. 7, 2007, in U.S. Appl. No. 10/197,077 (now U.S. Patent 7,320,999).
Amendment and Response under 37 C.F.R. § 1.111 filed Aug. 15, 2007, in U.S. Appl. No. 10/197,077 (now U.S. Patent 7,320,999).
Notice of Allowance mailed Aug. 28, 2007, in U.S. Appl. No. 10/197,077 (now U.S. Patent 7,320,999).
Preliminary Amendment filed May 10, 2001, in U.S. Appl. No. 09/831,620 (now U.S. Patent 6,509,376).
Office Action mailed Dec. 7, 2001, in U.S. Appl. No. 09/831,620 (now U.S. Patent 6,509,376).
Response filed Dec. 31, 2001, in U.S. Appl. No. 09/831,620 (now U.S. Patent 6,509,376).
Office Action mailed Mar. 4, 2002, in U.S. Appl. No. 09/831,620 (now U.S. Patent 6,509,376).
Response filed May 20, 2002, in U.S. Appl. No. 09/831,620 (now U.S. Patent 6,509,376).
Notice of Allowance mailed Aug. 30, 2002, in U.S. Appl. No. 09/831,620 (now U.S. Patent 6,509,376).
Interview Summary mailed May 14, 2008, in U.S. Appl. No. 11/765,578.
Response filed Apr. 14, 2008, in U.S. Appl. No. 11/765,578.
Interview Summary mailed Mar. 14, 2008, in U.S. Appl. No. 11/765,578.
Office Action mailed Dec. 14, 2007, in U.S. Appl. No. 11/765,578.
Supplemental Preliminary Amendment, filed Oct. 19, 2007, in U.S. Appl. No. 11/765,578.
Preliminary Amendment, filed Jun. 20, 2007, in U.S. Appl. No. 11/765,578.
Beljaards, "Ki-l-positive cutaneous lymphoreticular proliferations" British Journal of Dermatology (1990) 123: pp. 533-535.
de Haan, "The Risk of Sensibilization and Contact Urticaria upon Topical Application of Fumaric Acid Derivatives", Dermatology (1994) 188: pp. 126-130.
Nieboer et al., "Fumaric Acid Therapy in Psoriasis: A Double Blind Comparison between Fumaric Acid Compound Therapy and Monotherapy with Dimethylfumaric Acid Ester," Dermatologica (1990) 181: pp. 33-37.
Nieboer et al., "Treatment of Psoriasis with Fumaric Acid Derivatives", 239$^{th}$ N.S.D.V. Meeting, Br.J.Dermatol. (117, No. 6, 791-92, 1987).
Ros, et al., "Therapie bij psoriasis" Pharmaceutisch Weekblad (1991): 126 (13): 309-319.
van Loenen, et al., "Fumaarzuurtherapie: van fictie tot werkelijkheid?" Pharmaceutisch Weekblad (1989) 124: pp. 894-900.
Non-final Office Action mailed Sep. 15, 2008, in U.S. Appl. No. 11/765,578, filed Jun. 20, 2007.
Response filed Aug. 4, 2008, in U.S. Appl. No. 11/765,578, filed Jun. 20, 2007.
Final Office Action mailed Jul. 25, 2008, in U.S. Appl. No. 11/765,578, filed Jun. 20, 2007.
Applicant Summary of Interview filed Jun. 13, 2008, in U.S. Appl. No. 11/765,578, filed Jun. 20, 2007.

* cited by examiner

UTILIZATION OF DIALKYLFUMARATES

REFERENCE TO RELATED APPLICATIONS

This application is a divisional of application Ser. No. 10/197,077, filed Jul. 17, 2002 now U.S. Pat. No. 7,320,999, which is a divisional of application Ser. No. 09/831,620, filed May 10, 2001 now U.S. Pat. No. 6,509,376, which is a 371 continuation of PCT Application PCT/EP99/08215, filed Oct. 29, 1999, the text of which is not in English, which PCT Application claims priority on German Application No. 198 53 487.6, filed Nov. 19, 1998, the text of which is not in English, all of which are incorporated herein by reference.

DESCRIPTION

The present invention relates to the use of dialkyl fumarates for preparing pharmaceutical preparations for use in transplantation medicine or the therapy of autoimmune diseases and pharmaceutical preparations in the form of micro-tablets or micro-pellets containing dialkyl fumarates.

On the one hand, therefore, it relates especially to the use of dialkyl fumarates for preparing pharmaceutical preparations for the treatment, reduction or suppression of rejection reactions of the transplant by the recipient, i.e. host-versus graft reactions, or rejection of the recipient by the transplant, i.e. graft-versus-host reactions. On the other hand, it relates to the use of dialkyl fumarates for preparing pharmaceutical preparations for treating autoimmune diseases such as polyarthritis, multiple sclerosis, juvenile-onset diabetes, Hashimoto's thyroiditis, Grave's disease, systemic Lupus erythematodes (SLE), Sjogren's syndrome, pernicious anaemia and chronic active (=lupoid) hepatitis.

Both graft rejection and autoimmune diseases are based on medically undesirable reactions or dysregulation of the immune system. Cytokins such as interleukins or tumour necrose factor α (TNF-α) are substantial mediators influencing the immune system. In general, both are treated by the administration of immunosuppressive agents such as cyclosporine.

In the overall result, autoimmune diseases may be defined as the failure of the tolerance of endogenic substances or antigens. As a rule, this tolerance can be maintained only if the antigens keep coming into contact with immunological cells. When this tolerance is lost, autoantibodies are formed, i.e. a humoral immunoresponse against endogenic tissue. The exact nature of the involvement of TNF-α is not known.

Transplantations are tissue or organ transplantations, i.e. the transfer of tissues such as cornea, skin, bones (bone chips), vessels or fasciae, of organs such as kidney, heart, liver, lung, pancreas or intestines, or of individual cells such as islet cells, α-cells and liver cells, the kidney having the greatest significance as a transplanted organ.

According to the degree of relationship between the donor and the recipient we differentiate between autotransplantation (transfer to another part of the body of the same individual), iso-transplantation (transfer to another, genetically identical individual) and allogenic transplantation (transfer to another individual of the same species). Depending on the site of origin and transplantation, we further differentiate between homotopic transplantation (transfer to the same site) and heterotopic transplantation (transfer to a different site). The above-mentioned transplantations play an important role in modern medicine.

A major problem in transplantation medicine is graft rejection after transplantation of the tissue, organ or cell by immunological defense reactions of the recipient. Such a graft rejection is also called host-versus-graft reaction. The immunological defense reaction of the organism against the heteroprotein often results in rejection or dissolution of the grafts. In host-verses-graft reactions, different stages may be distinguished. Depending on the degree of difference between the recipient and the donor, this reaction takes place at different speeds so that we speak of an acute, sub-acute or chronic reaction. The acute rejection process is accompanied by the irreversible loss of the transplant (necrotisation) as a result of arteriitis or arteriolitis within 48 hours and cannot be influenced by the administration of drugs. The sub-acute rejection reaction becomes manifest as a rejection crisis from day 12 to month 4 with reversible functional disorders as a result of a transplant vasculopathy. Finally, the loss of function of the transplant as a result of vascular changes such as obliterating arteriopathy, which proceeds over weeks or years and can practically not be influenced by drugs, is termed a chronic rejection reaction.

Vice-versa, rejection reactions of the transplant against the recipient, the so-called graft-versus-host reactions, may occur when immunocompetent tissues are transplanted, i.e. primarily in bone marrow transplantation. Again, the severity of the reaction is graded, and substantially similar complications result as in host-versus-graft-reactions, namely arteriopathies and necroses.

To avoid such rejection reactions, i.e. the host-versus-graft reaction and the graft-versus-host reaction, transplantation medicine essentially makes use of immunosuppression, i.e. a weakening of the normal immunoresponse. For this purpose, anti-lymphocyte sera are often used in combination with corticosteroids and so-called anti-metabolites, e.g. purine analogues such as 6-mercaptopurine and thioguanine which affect the nucleic acid and protein synthesis and thus prevent cell division and proliferation. This leads to suppression of the production of antibodies and the cellular immune response. The immunosuppressive agents used for therapy are substances which suppress or weaken the immunoreaction in the body either specifically or non-specifically. Non-specific immunosuppressive agents are cytostatic agents such as, for example, alkylating agents or antimetabolites.

In addition, active 'ingredients are known which cause at least partial specific immunosuppression, such as corticosteroids, antisera, antibodies FK-506, tacrolimus, mycophenolatemofetil and primarily cyclosporines such as cyclosporine A. As a result of using modern immunosuppressive agents, the most important representatives of which are the cyclosporines, especially cyclosporine A, it was possible to improve the results of transplantation considerably over the last few years. At present, the survival rate after one year is about 60% for liver transplantations, about 80% for heart transplantations and over 90% for kidney transplantations.

Autoimmune diseases where the endogenic immune system attacks endogenic organs, tissues and cells are comparable to graft-versus-host reactions. These are also medically undesirable reactions of the immune system which may be treated with immunosuppressive agents, too.

The danger in using immunosuppressive agents lies in weakening the body's defense against infectious diseases and the increased risk of malignant diseases. Therefore, it is the object of the invention to provide a pharmaceutical preparation to be employed in transplantation medicine which may be used to treat, especially to suppress weaken and/or alleviate host-versus-graft reactions and graft-versus-host reactions, but does not have the above disadvantage.

It is another object of the invention to provide a pharmaceutical preparation which may be employed for treating autoimmune diseases, particularly polyarthritis, multiple sclerosis, juvenile-onset diabetes, Hashimoto's thyroiditis, Grave's disease, systemic Lupus erythematodes (SLE), Sjogren's syndrome, pernicious anaemia and chronic active (=lupoid) hepatitis, without the disadvantages of immunosuppression.

The object of the invention is achieved by using certain dialkyl fumarates for preparing pharmaceutical preparations for use in transplantation medicine and for the therapy of autoimmune diseases and pharmaceutical preparations in the form of micro-tablets and micro-pellets containing these dialkyl fumarates. The individual subject matters of the invention are characterized in detail in the claims. The preparations according to the invention do not contain any free fumaric acids per se.

It is known that pharmaceutical preparations which, upon biological degradation after administration, enter into the citric acid cycle or are part thereof gain increasing therapeutic significance—especially when given in high dosages—since they can alleviate or heal diseases caused cryptogenetically.

Fumaric acid, for example, inhibits the growth of the Ehrlich ascites tumour in mice, reduces the toxic effects of mitomycin C and aflatoxin and displays antipsoriatic and antimicrobial activity. When administered parenterally, transdermally and especially perorally, high dosages of fumaric acid or its derivatives known so far such as dihydroxyl fumaric acid, fumaramide and fumaronitrile have such unacceptably severe side effects and high toxicity that, in most cases, such a therapy had to be abandoned in the past.

Surprisingly, investigations carried out by the applicant have shown that methyl hydrogen fumarate, a metabolite of the dimethyl fumarate, initially increases the endotoxin-stimulated TNF-α secretion in human mononuclear cells of periphere blood (periphere blood mononuclear cells=PBMC cells) and in isolated monocytes. In addition, the applicant was able to show that fumaric acid has an effect on in vitro and in vivo haemagglutination which is comparable to that of cyclosporine.

Surprisingly, it has now been found that dialkyl fumarates are advantageous for preparing pharmaceutical compositions for use in transplantation medicine and for the therapy of autoimmune diseases. This is because compositions containing such dialkyl fumarates surprisingly permit a positive modulation of the immune system in host-versus-graft reactions, graft-versus-host reactions and other autoimmune diseases.

European Patent Application 0188 749 already describes fumaric acid derivatives and pharmaceutical compositions containing the same for the treatment of psoriasis. Pharmaceutical compositions for the treatment of psoriasis containing a mixture of fumaric acid and other fumaric acid derivatives are known from DE-A-25 30 372. The content of free fumaric acid is obligatory for these medicaments.

DE-A-26 21 214 describes medicaments containing the fumaric acid monoethyl ester and its mineral salts as active ingredient for the treatment of psoriasis. The publication "Hautarzt (Dermatologist) (1987) 279-285" discusses the use of fumaric acid monoethyl ester salts. Pharmaceutical preparations containing a mixture of fumaric acid monoalkyl ester salts and a fumaric acid diester for the treatment of psoriasis, psoriatic arthritis, neurodermatitis and enteritis regionalis Crohn are known from EP 0 312 697 B1.

Specifically, the object of the invention is achieved by the use of one or more dialkyl fumarates of the formula

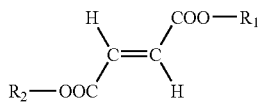

wherein $R_1$ and $R_2$, which may be the same or different, independently represent a linear, branched or cyclic, saturated or unsaturated $C_{1-20}$ alkyl radical which may be optionally substituted with halogen (Cl, F, I, Br), hydroxy, $C_{1-4}$ alkoxy, nitro or cyano for preparing a pharmaceutical preparation for use in transplantation medicine or for the therapy of autoimmune diseases.

The $C_{1-20}$ alkyl radicals, preferably $C_{1-8}$ alkyl radicals, most preferably $C_{1-5}$ alkyl radicals are, for example, methyl, ethyl, n-propyl, isopropyl, n-butyl, sec-butyl, t-butyl, pentyl, cyclopentyl, 2-ethyl hexyl, hexyl, cyclohexyl, heptyl, cycloheptyl, octyl, vinyl, allyl, 2-hydroxyethyl, 2 or 3-hydroxy propyl, 2-methoxy ethyl, methoxy methyl or 2- or 3-methoxy propyl. Preferably at least one of the radicals $R_1$ or $R_2$ is $C_{1-5}$ alkyl, especially methyl or ethyl. More preferably, $R_1$ and $R_2$ are the same or different $C_{1-5}$ alkyl radicals such as methyl, ethyl, n-propyl or t-butyl, methyl and ethyl being especially preferred. Most preferably, $R_1$ and $R_2$ are identical and are methyl or ethyl. Especially preferred are the dimethyl fumarate, methyl ethyl fumarate and diethyl fumarate.

The dialkyl fumarates to be used according to the invention are prepared by processes known in the art (see, for example, EP 0 312 697).

Preferably, the active ingredients are used for preparing oral preparations in the form of tablets, micro-tablets, pellets or granulates, optionally in capsules or sachets. Preparations in the form of micro-tablets or pellets, optionally filled in capsules or sachets are preferred and are also a subject matter of the invention. The oral preparations may be provided with an enteric coating. Capsules may be soft or hard gelatine capsules.

The dialkyl fumarates used according to the invention may be used alone or as a mixture of several compounds, optionally in combination with the customary carriers and excipients. The amounts to be used are selected in such a manner that the preparations obtained contain the active ingredient in an amount corresponding to 10 to 300 mg of fumaric acid.

Preferred preparations according to the invention contain a total amount of 10 to 300 mg of dimethyl fumarate and/or diethyl fumarate.

According to a preferred embodiment, the size or the mean diameter, respectively, of the pellets or micro-tablets is in the range from 300 to 2,000 μm, especially in the range of 500 or 1,000 μm.

In addition to graft-versus-host reactions (see above), the following autoimmune diseases to be treated may be named: polyarthritis, multiple sclerosis, graft-versus-host reactions, juvenile-onset diabetes, Hashimoto's thyroiditis, Grave's disease, systemic Lupus erythematodes (SLE), Sjogren's syndrome, pernicious anaemia and chronic active (lupoid) hepatitis. Autoimmune diseases in a wider meaning also comprise psoriasis, psoriatic arthritis, neurodermatitis and enteritis regionalis Crohn.

In addition to the preparations for peroral administration in the form of micro-pellets, micro-tablets, capsules (such as soft and hard gelatine capsules), granulates and tablets cited above, suitable pharmaceutical preparations are preparations for cutaneous and transdermal administration in the form of ointments, plasters, lotions or shower preparations and for parenteral administration in the form of aqueous micro-dispersions, oil-in-water emulsions or oily solutions for rectal administration of suppositories or micro-enemas. Pharmaceutical preparations in the form of micro-tablets or micro-pellets are preferred for the therapy of all autoimmune diseases mentioned above, including psoriasis, psoriatic arthritis, neurodermatitis and enteritis regionalis Crohn and are also a subject matter of the invention.

According to the invention, a therapy with dialkyl fumarates may also be carried out in combination with one or more preparations of the triple drug therapy customarily used in organ transplantations or with cyclosporine A alone. For this purpose, the preparations administered may contain a combination of the active ingredients in the known dosages or amounts, respectively. Likewise, the combination therapy may consist of the parallel administration of separate preparations, by the same or different routes. Optionally, the dosage of the active ingredient contained in addition to the dose of the fumaric acid derivative administered in accordance with the invention may be reduced advantageously.

Another embodiment of the use according to the invention is to alternate the drug therapy with immunosuppressive agents such as cyclosporine in sequence with an application of the above-mentioned dialkyl fumarate. This means that an application of fumaric acid derivatives as defined above over one or more weeks may follow a cyclosporine therapy of one or more weeks. This permits reduction of the Cyclosporine A dosage resulting in a considerable decrease of the rate of side effects in long-term therapy.

By administration of the dialkyl fumarates in the form of micro-tablets, which is preferred, gastrointestinal irritations and side effects, which are reduced already when conventional tablets are administered but is still observed, may be further reduced vis-a-vis fumaric acid derivatives and salts.

It is presumed that, upon administration of conventional tablets, the ingredients of the tablet are released in the intestine in a concentration which is too high, causing local irritation of the intestinal mucous membrane. This local irritation results in a short-term release of very high TNF-$\alpha$ concentrations which may be responsible for the gastrointestinal side effects. In case of application of enteric-coated micro-tablets in capsules, on the other hand, very low local concentrations of the active ingredients in the intestinal epithelial cells are achieved. The micro-tablets are incrementally released by the stomach and passed into the small intestine by peristaltic movements so that distribution of the active ingredients is improved.

This means that enteric-coated micro-tablets in the same dosage are distributed already in the stomach and passed to the intestine in portions, where the active ingredients are released in smaller dosages. This avoids local irritation of the intestinal epithelial cells and the release of TNF-$\alpha$. It is assumed that this results in the improved tolerance of micro-tablets in the gastrointestinal tract vis-a-vis conventional tablets.

In addition, resorption is improved, because the dialkyl fumarates to be used according to the invention are not the active ingredient per se, but a so-called prodrug, which must be converted into the active ingredient in the body.

In order to illustrate the use according to the invention, different examples for preparing preferred drugs are given below.

PRODUCTION EXAMPLES

In principle, the oral preparations according to the invention in the form of tablets or micro-tablets may be prepared by classical tabletting processes. Instead of such classical tabletting processes, other methods for the preparation of tablets may be used, such as direct tabletting and processes for preparing solid dispersions in according with the melt method and the spray drying method.

The tablets may be provided with an enteric coating. The enteric coating may be applied in a classical coating pan or sprayed on or applied in a fluidised bed apparatus. The tablet may also be provided with a film coat.

Example 1

Preparation of Enteric-Coated Micro-Tablets in Capsules Containing 120.0 mg of Dimethyl Fumarate, which Corresponds to 96 mg of Fumaric Acid Taking the necessary precautions (breathing mask, gloves, protective clothing, etc.), 12.000 kg of dimethyl fumarate are crushed, mixed and homogenized by means of a sieve 800. Then an excipient mixture with the following composition is prepared: 17.50 kg of starch derivative (STA-RX® 1500), 0.30 kg of microcrystalline cellulose (Avicel® PH 101), 0.75 kg of PVP (Kollidon® 120), 4.00 kg of Primogel®, 0.25 kg of colloidal silicic acid (Aerosil®). The active ingredient is added to the entire powder mixture, mixed, homogenized by means of a sieve 200, processed in the usual manner with a 2% aqueous solution of polyvidon pyrrolidone (Kollidon® K25) to obtain a binder granulate and then mixed in the dry state with the outer phase. Said outer phase consists of 0.50 kg of Mg stearate and 1.50 kg of talcum.

Then the powder mixture is compressed in the usual manner to obtain convex tablets having a gross weight of 10.0 mg and a diameter of 2.0 mm.

One example to achieve resistance to gastric acid is to dissolve a solution of 2.250 kg of hydroxy propyl methyl cellulose phthalate (HPMCP, Pharmacoat® HP 50) in portions in a mixture of the following solvents: 13.00 l of acetone, 13.50 l of ethanol (94 wt.-%, denatured with 2% of ketone) and 1.50 l of demineralised water. As a plasticiser, castor oil (0.240 kg) is added to the finished solution and applied in portions onto the tablet cores in the customary manner.

After drying is completed, a suspension of the following composition is applied as a film coat in the same apparatus: 0.340 kg of talcum, 0.400 kg of titanium(VI) oxide Cronus RN 56, 0.324 kg of coloured lacquer L-Rot-lack 86837, 4.800 kg of Eudragit E 12.5% and 0.120 kg of polyethylene glycol 6000, pH 11 XI in a solvent mixture of the following composition: 8.170 kg of 2-propanol, 0.200 kg of demineralised water and 0.600 kg of glycerine triacetate (Triacetin).

After that the enteric-coated micro-tablets are filled into hard gelatine capsules having a net weight of 400 mg and sealed.

Example 2

Preparation of Enteric-Coated Micro-Tablets in Capsules Containing 120.0 mg of Dimethyl Fumarate, which Corresponds to 96 mg of Fumaric Acid 12.000 kg of dimethyl fumarate are crushed and homogenized as above. Then an excipient mixture composed as follows is prepared: 23.20 kg of microcrystalline cellulose (Avicel® PH 200), 3.00 kg of Croscarmellose sodium (AC-Di-SOL-SD-711), 2.50 kg of talcum, 0.10 kg of anhydrous silica (Aerosil 200) and 1.00 kg of Mg stearate. The active ingredient is then added to the entire powder mixture and mixed homogenously. By means of direct tabletting, the powder mixture is then pressed into convex tablets having a gross weight of 10.0 mg and a diameter of 2.00 mm.

After that, a solution of 0.94 Eudragit® L in isopropanol is prepared which also contains 0.07 kg of dibutyl phthalate. This solution is sprayed onto the tablet cores. After that, a dispersion of 17.32 kg of Eudragit® L D-55 and a mixture of 2.80 kg of microtalcum, 2.00 kg of Macrogol 6000 and 0.07 kg of dimeticon in water is prepared and sprayed onto the cores.

Next, the enteric-coated micro-tablets are filled into hard gelatine capsules having a net weight of 650 mg and sealed.

Example 3

Preparation of Micro-Pellets in Capsules Containing 50.0 mg of Dimethyl Fumarate, which Corresponds to 40 mg of Fumaric Acid 5.000 kg of dimethyl fumarate are crushed and homogenized as above. In addition, 21 of a 20% (m/v) polyvinyl pyrrolidone solution (Kollidon K-30) in ethanol are prepared. 7.250 kg of nonpareilles pellets in a coating pan are sprayed with part of the Kollidon K-30 solution until slightly humid. Then the active ingredient is added in portions until the pellets are dry. This procedure of humidification/drying is continued until all of the active ingredient mixture has been added. Then the pellets are moved around until completely dry.

After that, the pellets are filled into hard gelatine capsules (126.5 mg pellets/capsule).

Example 4

Preparation of Enteric-Coated Capsules Containing 110.0 mg of Dimethyl Fumarate, which Corresponds to 88 mg of Fumaric Acid 11.000 kg of dimethyl fumarate are intensely mixed in a mixture consisting of 14.00 kg of starch, 5.65 kg of lactose, 2.00 kg of microcrystalline cellulose (Avicel®), 1.00 kg of polyvinyl pyrrolidone (Kollidon® 25) and 2.443 kg of Primogel® and, taking the necessary precautions (breathing mask, gloves, protective clothing), homogenized by means of a sieve 800.

Using a 2% aqueous solution of polyvinyl pyrrolidone (Kollidon® K25), the entire powder mixture is processed into a binder granulate in the customary manner and mixed with the outer phase when dry. Said outer phase consists of 0.350 kg of colloidal silicic acid (Aerosil®), 0.500 kg of Mg stearate and 1.500 kg of talcum. The homogenous mixture is filled into suitable capsules in portions of 400 mg which are then provided with an enteric coating consisting of hydroxy propyl methyl cellulose stearate and castor oil as plasticiser in the customary manner. Instead of using hard gelatine capsules, the product may also be filled into suitable enteric-coated capsules consisting of a mixture of cellulose acetate phthalate (CAP) and hydroxy propyl methyl cellulose phthalate (HP-MCP).

In comparison with substances of the prior art such as cyclosporine, which may cause massive kidney disorders or diseases of the lymphoproliferative system, a therapy with fumaric acid derivatives according to the invention for the indications listed above rarely results in serious side effects.

Among other things, the immunosuppressive effect of cyclosporine is caused by the inhibition of Th-1 cell formation. As in vitro experiments of the applicant have shown, fumarates cause a shift of the cytokine pattern of the Th1 type to the cytokine pattern of the Th2 type.

Especially in view of the long-term therapy and prevention which is always necessary in graft-versus-host reactions and host-versus-graft reactions or other autoimmune diseases such as multiple sclerosis, the unexpected effect of the use according to the invention is of the greatest interest. In a combination therapy of cyclosporine with the fumaric acid derivatives, the toxic side effects of the former compounds may be unexpectedly reduced to a substantial degree. In addition, the use according to the invention is also significant in the substitution of the corticosteroid therapy of autoimmune diseases which is known to be accompanied by severe side effects.

That which is claimed is:

1. A method of treating autoimmune polyarthritis but not treating psoriatic arthritis, comprising administering, to a patient in need of treatment for said polyarthritis but not for said psoriatic arthritis, an amount of a pharmaceutical preparation effective for treating said polyarthritis, the pharmaceutical preparation comprising
    at least one excipient or at least one carrier or a combination thereof and
    an active ingredient only consisting of dimethyl fumarate, methyl hydrogen fumarate, or a combination thereof.
2. The method of claim 1, wherein 10 mg to 300 mg of the active ingredient is administered.
3. The method of claim 1, wherein the active ingredient is provided in one or more capsules.
4. The method of claim 1, wherein the active ingredient consists of 50 mg of dimethyl fumarate.
5. The method of claim 1, wherein the active ingredient consists of 110 mg of dimethyl fumarate.
6. The method of claim 1, wherein the active ingredient consists of 120 mg of dimethyl fumarate.
7. The method of claim 1, wherein the active ingredient consists of methyl hydrogen fumarate.
8. The method of claim 7, wherein the active ingredient consists of 10 mg to 300 mg of methyl hydrogen fumarate.
9. The method of claim 1, wherein the active ingredient consists of dimethyl fumarate.
10. The method of claim 9, wherein the active ingredient consists of 10 mg to 300 mg of dimethyl fumarate.
11. The method of claim 9, wherein the active ingredient consists of 50 mg of dimethyl fumarate.
12. The method of claim 9, wherein the active ingredient consists of 110 mg of dimethyl fumarate.
13. The method of claim 9, wherein the active ingredient consists of 120 mg of dimethyl fumarate.
14. The method of claim 1, wherein the pharmaceutical preparation is formulated for oral administration.
15. The method of claim 1, wherein the pharmaceutical preparation is formulated as a solid dosage form.
16. The method of claim 1, wherein the pharmaceutical preparation is in the form of microtablets.
17. The method of claim 16, wherein the microtablets are provided in one or more capsules, each capsule containing at least 50 mg of dimethyl fumarate.
18. The method of claim 17, wherein each capsule contains at least 110 mg of dimethyl fumarate.
19. The method of claim 18, wherein each capsule contains at least 120 mg of dimethyl fumarate.
20. The method of claim 16, wherein the microtablets are enteric-coated.

21. The method of claim 16, wherein the microtablets have a mean diameter in the range of 0.3 mm to 2.0 mm, exclusive of any coating on the microtablets.

22. The method of claim 21, wherein the microtablets have a mean diameter of 2.0 mm, exclusive of any coating on the microtablets.

23. The method of claim 1, wherein the active ingredient consists of at least 50 mg of dimethyl fumarate.

24. The method of claim 1, wherein the active ingredient consists of at least 110 mg of dimethyl fumarate.

25. The method of claim 1, wherein the active ingredient consists of at least 120 mg of dimethyl fumarate.

26. The method of claim 1, wherein the pharmaceutical preparation comprises at least one carrier.

27. The method of claim 1, wherein the pharmaceutical preparation comprises at least one excipient.

28. The method of claim 1, wherein the active ingredient consists of only both dimethyl fumarate and methyl hydrogen fumarate.

29. The method of claim 1, wherein the pharmaceutical preparation comprises at least one excipient and at least one carrier.

* * * * *